United States Patent
Doshi et al.

(10) Patent No.: US 9,034,363 B2
(45) Date of Patent: May 19, 2015

(54) DRUG-ELUTING INSERTABLE MEDICAL DEVICE FOR TREATING ACUTE MYOCARDIAL INFARCTION, THROMBUS CONTAINING LESIONS AND SAPHENOUS-VEIN GRAFT LESIONS

(75) Inventors: Manish Doshi, Surat (IN); Divyesh Sherdiwala, Surat (IN); Prakash Sojitra, Surat (IN)

(73) Assignee: CONCEPT MEDICAL RESEARCH PRIVATE LIMITED, Surat (IN)

( * ) Notice: Subject to any disclaimer, the term of this patent is extended or adjusted under 35 U.S.C. 154(b) by 0 days.

(21) Appl. No.: 13/124,124
(22) PCT Filed: Jan. 6, 2011
(86) PCT No.: PCT/IN2011/000007
§ 371 (c)(1),
(2), (4) Date: Apr. 13, 2011
(87) PCT Pub. No.: WO2011/089618
PCT Pub. Date: Jul. 28, 2011

(65) Prior Publication Data
US 2012/0277726 A1    Nov. 1, 2012

(30) Foreign Application Priority Data
Jan. 22, 2010   (IN) .......................... 177/MUM/2010

(51) Int. Cl.
*A61L 29/16* (2006.01)
*A61K 9/127* (2006.01)
(Continued)

(52) U.S. Cl.
CPC ............... *A61L 29/16* (2013.01); *A61K 9/127* (2013.01); *A61L 31/16* (2013.01); *A61L 2300/41* (2013.01);
(Continued)

(58) Field of Classification Search
USPC .................. 604/500, 509, 103.02; 623/1.11; 424/424
See application file for complete search history.

(56) References Cited

U.S. PATENT DOCUMENTS

2005/0055078 A1   3/2005 Campbell
2007/0207186 A1*  9/2007 Scanlon et al. .............. 424/424
(Continued)

FOREIGN PATENT DOCUMENTS

CN   1647776     8/2005
CN   1883720    12/2006
(Continued)

OTHER PUBLICATIONS

"International Search Report dated Aug. 11, 2011", PCT Application No. PCT/IN2011/000007, 5 pages.

*Primary Examiner* — Nicholas Lucchesi
*Assistant Examiner* — Melissa A Snyder
(74) *Attorney, Agent, or Firm* — Timberline Patent Law Group PLLC (57) ABSTRACT

A method for delivering at least one drug at a target site in a blood vessel for treating at least one of an acute myocardial infarction, a thrombus containing lesion and a saphenous-vein graft lesion is disclosed. The method includes delivering nano-carriers at the target site. The nano-carriers include one or more drugs encapsulated with a first biological agent. The nano-carriers further include a second biological agent in contact with one or more of the first biological agent and the one or more drugs. The first biological agent and the second biological agent have a first dissolution rate and a second dissolution rate respectively. The first dissolution rate is different from the second dissolution rate. The one or more drugs are released at the target site from the nano-carriers at a first release rate and a second release rate in response to dissolution of the first biological agent and the second biological agent, respectively.

6 Claims, 3 Drawing Sheets

(51) Int. Cl.
*A61L 31/16* (2006.01)
*A61M 31/00* (2006.01)
*A61M 25/00* (2006.01)
*A61M 25/10* (2013.01)

(52) U.S. Cl.
CPC ........ *A61L 2300/42* (2013.01); *A61L 2300/604* (2013.01); *A61L 2300/624* (2013.01); *A61M 31/00* (2013.01); *A61M 2025/0057* (2013.01); *A61M 2025/105* (2013.01)

(56) References Cited

U.S. PATENT DOCUMENTS

2007/0299510 A1\* 12/2007 Venkatraman et al. ...... 623/1.44
2009/0304772 A1\* 12/2009 Choubey et al. .............. 424/423

FOREIGN PATENT DOCUMENTS

EP          1977772         10/2008
WO     WO-2007140320       12/2007

\* cited by examiner

FIG. 3

DRUG-ELUTING INSERTABLE MEDICAL DEVICE FOR TREATING ACUTE MYOCARDIAL INFARCTION, THROMBUS CONTAINING LESIONS AND SAPHENOUS-VEIN GRAFT LESIONS

FIELD OF THE INVENTION

The invention generally relates to a method and a drug-eluting insertable medical device for treating Acute Myocardial Infarction (AMI), Thrombus Containing Lesion (TCL) and Saphenous Vein Graft Lesion (SVGL). More specifically, the invention relates to a drug-eluting insertable medical device coated with nano-carriers for releasing the drug at different rates to address acute thrombus formation, sub-acute thrombus formation and late thrombus formation otherwise associated with treatment of AMI, TCL and SVGL.

BACKGROUND OF THE INVENTION

Acute Myocardial Infarction (AMI), Thrombus Containing Lesion (TCL) and Saphenous Vein Graft Lesion (SVGL) are currently treated by techniques such as Percutaneous Transluminal Coronary Angioplasty (PTCA). Generally, Drug-eluting Stents (DESs), balloon catheters and Bare Metal Stents (BMSs) are used in PTCA. In addition, thrombus aspiration catheters are also used for treating TCL. The thrombus aspiration catheters retrieve a thrombus from a blood vessel and drain the thrombus out of a patient's blood stream.

Generally, polymers are used for loading the drugs onto the DESs. The polymers used in the DESs may lead to inflammation as a result of body's immune response to the polymers. Further, depending upon the properties of the polymers, the polymers used in the DESs may result in acute thrombus formation, sub-acute thrombus formation and late thrombus formation. The thrombus formed may further aggravate that may lead to blocking of the blood vessel thereby resulting in restenosis. Further, blocking of the blood vessel results in "slow-flow" and "no-flow" in patients suffering from AMI and TCL.

In addition to the DESs, the balloon catheters are also used for performing the PTCA for treating AMI, TCL and SVGL. However, the balloon catheters cause disruption of internal layers of the blood vessels and stretching of the blood vessels. The disruption of internal layers may lead to an acute thrombus formation, a sub-acute thrombus formation and a late thrombus formation. Whereas, the stretching of the blood vessel may result in inflammation. Further, stretching and the inflammation of the blood vessel may lead to restenosis. Thus, the sub-acute thrombus formation and the late thrombus formation may not be avoided when the balloon catheters are used.

Another insertable medical device used to perform PTCA for treating AMI, TCL and SVGL are the BMSs. However, the BMSs may also cause development of inflammation at the site of deployment as a result of body's immune response. The BMSs may rupture tissues of the blood vessels resulting in acute thrombus formation. The acute thrombus formation may further progress to a sub-acute thrombus and a late thrombus. Patients suffering from AMI, TCL and SVGL when treated with the DESs are observed to be more vulnerable to re-occurrence of lesions and thrombus as compared to patients treated with the BMSs and the balloon catheters.

Therefore, there is a need in the art for an improved drug-eluting insertable medical device for treating AMI, TCL and SVGL to overcome acute inflammation of the blood vessels resulting in thrombus formation. Further, in order to minimize the condition of "slow-flow" and "no-flow" of blood in patients suffering from AMI and TCL, an improved drug-eluting insertable medical device is needed in the art. Moreover, there is a need in the art for an improved drug-eluting insertable medical device to deliver an anti-inflammatory agent and an anti-thrombogenic agent without using polymers used for loading the drugs on the drug-eluting insertable medical device.

DETAILED DESCRIPTION OF THE INVENTION

Before describing in detail embodiments that are in accordance with the invention, it should be observed that the embodiments reside primarily in combinations of components of a drug-eluting insertable medical device and method steps for delivering one or more drugs at a target site using the drug-eluting insertable medical device. Accordingly, the components of the drug-eluting insertable medical device and the method steps have been described to include only those specific details that are pertinent to understanding the embodiments of the invention so as not to obscure the disclosure with details that will be readily apparent to those of ordinary skill in the art having the benefit of the description herein.

In this document, the terms "comprises," "comprising," or any other variation thereof, are intended to cover a non-exclusive inclusion, such that a process, method, device or article, that comprises a list of elements does not include only those elements but may include other elements not expressly listed or inherent to such process, method, article, or apparatus. An element preceded by "comprises . . . a" does not, without more constraints, preclude the existence of additional identical elements in the process, method, device or article that comprises the element.

Further, before describing in detail embodiments that are in accordance with the invention, it should be observed that all the scientific and technical terms used in for describing the invention have same meanings as would be understood by a person skilled in the art.

Various embodiments of the invention provide a method for delivering one or more drugs at a target site in a blood vessel for treating one of Acute Myocardial Infarction (AMI), Thrombus Containing Lesion (TCL), and Saphenous-Vein Graft Lesion (SVGL). The method includes positioning a drug-eluting insertable medical device coated with nano-carriers at the target site. The nano-carriers include one or more drugs encapsulated with a first biological agent having a first dissolution rate. The nano-carriers further include a second biological agent in contact with one or more of the first biological agent and the one or more drugs. The second biological agent has a second dissolution rate. The first dissolution rate differs from the second dissolution rate.

Upon positioning the drug-eluting insertable medical device at the target site, the nano-carriers are discharged from the drug-eluting insertable medical device. Thereafter, dissolution of the first biological agent and the second biological agent takes place at the first dissolution rate and the second dissolution rate, respectively. Subsequently, the one or more drugs are released at the target site from the nano-carriers in response to dissolution of the first biological agent and the second biological agent, respectively.

Thus, owing to different dissolution rates of the first biological agent and the second biological agent, release of the one or more drugs from the nano-carriers takes place at different times and different rates. For example, a first portion of the one or more drugs may be released at a first release rate in response to dissolution of the first biological agent. Whereas, a second portion of the one or more drugs may be released at a second release rate upon dissolution of the second biological agent. The second release rate is greater than the first release rate. As such, the one or more drugs released at the second rate address acute thrombus formation and the one or more drugs released at the first release rate address one or more of a sub-acute thrombus formation and a late thrombus formation. Therefore, the method may be used to effectively treat one or more of AMI, TCL and SVGL.

Figure 1:
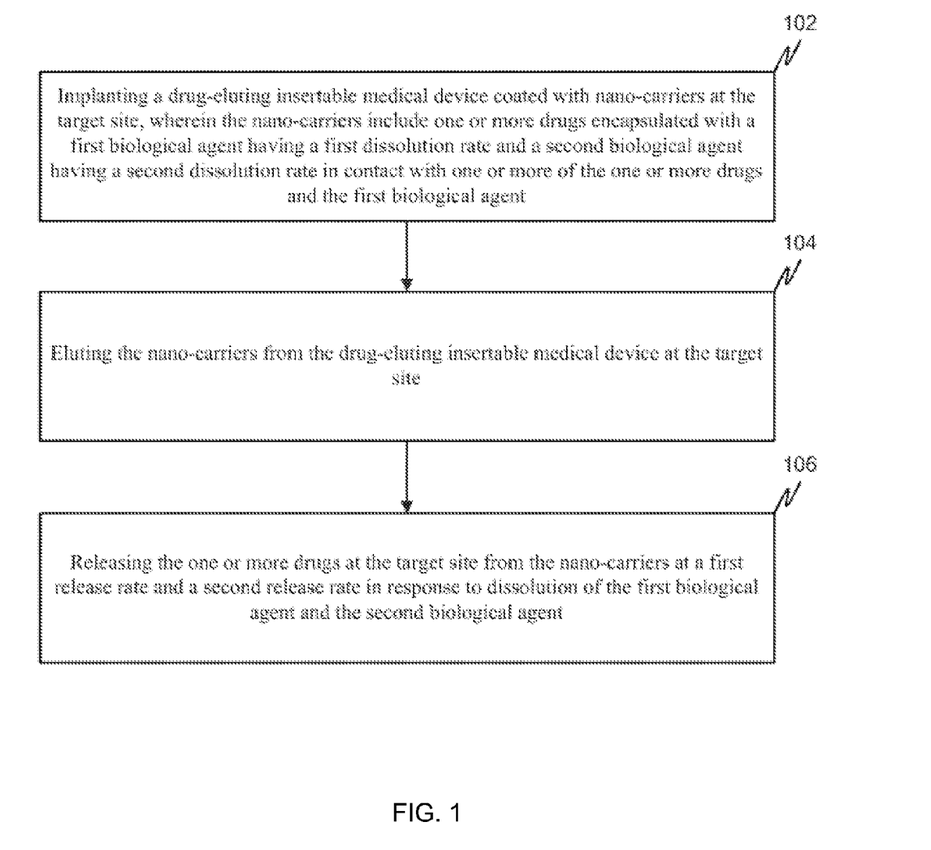
FIG. 1 illustrates a flow chart of a method for delivering one or more drugs at a target site in a blood vessel using a drug-eluting insertable medical device in accordance with an embodiment of the invention.

FIG. 1 illustrates a flow chart of a method for delivering one or more drugs at a target site in a blood vessel using a drug-eluting insertable medical device in accordance with an embodiment of the invention. The drug-eluting insertable medical device is positioned at the target site in the blood vessel at step 102. The drug-eluting insertable medical device may be positioned at the target site using methods and techniques known in the art. The target site may include, for example, but is not limited to a lesion and a thrombus in the blood vessel of a patient suffering from one or more of AMI, TCL and SVGL. Examples of the blood vessel may include, but are not limited to, a coronary artery, a peripheral artery, a carotid artery, a renal artery, an illiac artery, an artery below a knee, and a vein.

In an embodiment, the blood vessel is a coronary artery. In this case, the drug-eluting insertable medical device is positioned at the target site in the coronary artery. Examples of the drug-eluting insertable medical device may include, but are not limited to, a stent, a balloon catheter, a catheter balloon and a thrombus aspiration catheter. Any other medical device may be used for delivering the one or more drugs at the target site without departing from the scope of the invention. The drug-eluting insertable medical device is coated with nano-carriers. The nano-carriers include one or more drugs encapsulated with a first biological agent. The nano-carriers further include a second biological agent in contact with one or more of the first biological agent and the one or more drugs. The second biological agent has a second dissolution rate. The first dissolution rate differs from the second dissolution rate.

Examples of the one or more drugs may include, but are not limited to, a dexamethasone, a genistine, a flavenoid, a neoflavone, a aurone, a chalcone, a dihydrochalcone, a flavonol, a dihydroflavonol, a flavone, a isoflavone, a anthocyanidin, a proanthocyanidin, a isoflavane, a beta-estradiol, a sulphated glycosaminoglycan, heparin, heparin sulphate, dermatan sulphate, chondroitin sulphate, a derivative or conjugate of sulphated glycosaminoglycan, an anti-thrombin, an anti-proliferative agent, metotrexate, mitomycin C, doxyrubicin, a somatostatin analog, cytoschalasin B, rapamycin, cyclosporin, glucocorticoid (e.g. dexamethasone, betamethasone), hirudin, a tocopherol, an angiopeptin, dexamethasone sodium phosphate, a thrombin modulator such as pyridine, pyridine N-oxide, methylprednisolone, sulfasalazine, vincristine, vinblastine, fluorouracil, doxorubicin hydrochloride, an anticoagulant, an antifibrin, an antithrombin, sodium heparin, a low molecular weight heparin, a heparinoid, hirudin, argatroban, forskolin, vapiprost, a prostacyclin, a prostacyclin analogue, dextran, a D-phe-pro-arg-chloromethylketone (synthetic antithrombin), dipyridamole, a glycoprotein IIIb/IIIa platelet membrane receptor antagonist, an antibody, a recombinant hirudin, bivalirudin, an angiopeptin, an antimitotic agent, and an oligonucleotide. In an embodiment, the one or more drugs are Dexamethasone.

The first biological agent and the second biological agent may be selected from one or more of, but are not limited to, a drug carrier, a blood component, a phospholipid, a solid lipid nano-particle, a lipoid, a vitamin, and a sugar molecule. Examples of the first biological agent and the second biological agent may include, but are not limited to, a steroid, an estradiol, an esterified fatty acid, a non esterified fatty acid, a glucose, an inositol, a L-lactate, a lipoprotein, a carbohydrate, a tricalcium, a phosphate, a precipitated calcium phosphate, a calcium phoshate tribasic, substances derived from at least one of a human, an egg, a soybean, a phospholipon 80H, a phospholipon 90H, a lipoid S75, a lipoid E80, an intralipid 20, a lipoid EPC, a lipoid E75, a lipid obtained from egg, a lipid obtained from soya, a phosphatidylcholine, a phosphatidylglycerol, a phosphatidylinositol, a phosphatidylserine, a phosphatidic acid, a cardiolipin, and a phosphatidylethanolamine. In an embodiment, the first biological agent is Lipoid E80 and the second biological agent is tricalcium phosphate.

In response to positioning the drug-eluting insertable medical device at the target site, the nano-carriers are discharged from the drug-eluting medical device at step 104. Thereafter, the first biological agent and the second biological agent come in contact with a body fluid at the target site. Once the contact is established with the body fluid, dissolution of the first biological agent and the second biological agent may be initiated. Thereafter, the one or more drugs are released at the target site from the nano-carriers in response to dissolution of the first biological agent and the second biological agent respectively at step 106.

In accordance with various embodiments, the first biological agent and the second biological agent have different dissolution rates. For example, the first biological agent may have a first dissolution rate and the second biological agent may have a second dissolution rate. Further, the second dissolution rate may be greater than the first dissolution rate. Thus, a first portion of the one or more drugs are released from the nano-carriers in response to dissolution of the second biological agent at the target site. The nano-carriers may thus provide a burst or rapid release of the one or more drugs. The first portion of the one or more drugs thus released from the nano-carriers address the acute thrombus formation. Whereas, a remaining second portion of the one or more drugs is released from the nano-carriers in response to dissolution of the first biological agent. The second portion of the one or more drugs released from the nano-carriers may thus provide a prolonged or delayed release of the one or more drugs. The second portion of the one or more drugs released from the nano-carriers address the sub-acute thrombus formation or the late thrombus formation.

Various embodiments of the invention may also provide a drug-eluting insertable medical device for delivering the one or more drugs at the target site in the blood vessel for treating one or more of AMI, TCL and SVGL. The drug-eluting insertable medical device includes a surface coated with the nano-carriers.

The nano-carriers include the one or more drugs encapsulated with the first biological agent having the first dissolution rate. The nano-carriers further include a second biological agent in contact with one or more of the first biological agent and the one or more drugs. The second biological agent has a second dissolution rate. The first dissolution rate differs from the second dissolution rate. This is explained in detail in conjunction with FIG. 1.

In an embodiment, the drug-eluting insertable medical device includes an outer surface and an inner surface. The outer surface of the drug-eluting insertable medical device comes in contact with the target site of the blood vessel to deliver the nano-carriers. Therefore, only the outer surface of the drug-eluting insertable medical device is coated with the nano-carriers. Whereas, the inner surface of the drug-eluting insertable medical device is substantially devoid of the nano-carriers.

In an embodiment, the drug-eluting insertable medical device is a Drug-Eluting Balloon (DEB). The DEB coated with the nano-carriers is inserted into the blood vessel and positioned at the target site. The target site may include a lesion or a thrombus in the blood vessel of a patient suffering from one or more of AMI, TCL and SVGL. The DEB upon inflation at the target site comes in contact with the lesion. Upon contact with the lesion, the nano-carriers are eluted from an outer surface of the DEB at the target site.

The first portion of the one or more drugs present in the nano-carriers are released at the target site before the second portion of the one or more drugs present in the nano-carriers based on the dissolution rate of the first biological agent and the second biological agent. The release of the one or more drugs at the target site from the nano-carriers are proportional to the first dissolution rate and the second dissolution rate respectively.

Further, the first biological agent and the second biological agent may exhibit one or more properties. The one or more properties may include, but are not limited to, one or more of stabilizing the nano-carriers and affinity for tissues of the target site in the blood vessel. The first biological agent and the second biological agent may dissolve at different pH values to exhibit a different rate of release of one or more drugs from the first set of nano-carriers and the second set of nano-carriers. For example, the second biological agent, such as, tricalcium phosphate, may dissolve in a pH below 7.4. Accordingly, when the nano-carriers come in contact with the blood at the target site, the second biological agent may dissolve. In response to dissolution of the second biological agent, a first portion of the one or more drugs is released from the nano-carriers. Whereas, a remaining second portion of the one or more drugs is released from the nano-carriers upon dissolution of the first biological agent. Thus, the first portion and the second portion of the one or more drugs present in the nano-carriers may exhibit different release profiles to address different phases of one or more of AMI, TCL and SVGL.

Thus, the first portion of the one or more drugs released from the nano-carriers exhibit a burst release to address acute thrombus formation. Whereas, the second portion of the one or more drugs released from the nano-carriers exhibit a prolonged in-tissue release to address sub-acute thrombus formation and late-thrombus formation occurring at the target site.

For example, the nano-carriers may include one or more of an anti-thrombogenic agent and an anti-inflammatory agent encapsulated with the first biological agent. The nano-carriers may further include the second biological agent in contact with one or more of the one or more drugs and the first biological agent. The second biological agent may have a rapid dissolution rate thereby exhibiting a burst release of the one or more drugs, such as, the anti-thrombogenic agent. The first biological agent may have a slow dissolution rate thereby exhibiting a prolonged release of the anti-inflammatory agent. Various combinations of the first biological agent and the second biological agent having different dissolution rates may be used to achieve desired release profiles of the one or more drugs without departing from the scope of the invention.

In another embodiment, the nano-carriers include a first set of nano-carriers and a second set of nano-carriers. The first set of nano-carriers includes the one or more drugs encapsulated with the first biological agent. The second set of nano-carriers includes the one or more drugs encapsulated with the first biological agent. Alternatively, the first set of nano-carriers may include a first drug and the second set of nano-carriers may include a second drug. The first drug and the second drug may be same or different. For example, the first drug and the second drug may include one or more of, but are not limited to, an anti-inflammatory agent and an anti-thrombogenic agent.

The first set of nano-carriers and the second set of nano-carriers may have two or more different average diameters. The two or more average diameters may range from 1 nm to 5000 nm. For example, the first set of nano-carriers may have a first average diameter and the second set of nano-carriers may have a second average diameter. The first average diameter may be different from the second average diameter. The two or more average diameters of the first set of nano-carriers and the second set of nano-carriers are suitable for penetrating one or more layers of the blood vessel to achieve in-tissue penetration of the one or more drugs at the target site. Any number of different sets of the nano-carriers with varying average diameters may be used to achieve a particular therapeutic objective without departing from the scope of the invention. The therapeutic objective may include penetrating one or more layers of the blood vessel to achieve in-tissue penetration of the drug at the target site. In-tissue penetration of the drug provides a prolonged release of the one or more drugs for a prolonged therapeutic effect.

Once first set of nano-carriers and the second set of nano-carriers are transferred to the target site, these sets of nano-carriers penetrate the one or more layers of the blood vessel. For example, the first set of nano-carriers may directly penetrate an intima layer of the blood vessel after the nano-carrier is released from the outer surface. However, for the second set of nano-carriers to penetrate the media layer and the adventitia layer, the second set of nano-carriers may pass through vasa vasorum associated with the media layer and the adventitia layer. The first set of nano-carriers and the second set of nano-carriers can penetrate one or more layers of the blood vessel depending upon an average diameter associated with the first set of nano-carriers and the second set of nano-carriers. For example, when the average diameter of the second set of nano-carriers ranges between 10 nm to about 300 nm, the second set of nano-carriers can penetrate up to the adventitia layer via passing through the intima layer, a vasa vasorum associated with the media layer and a vasa vasorum associated with the adventitia layer.

In yet another embodiment, the first set of nano-carriers may have a first average diameter and includes the one or more drugs encapsulated with the first biological agent. The first set of nano-carriers may further include the second biological agent in contact with one or more of the one or more drugs and the first biological agent. Further, the second set of nano-carriers may have a second average diameter and includes the one or more drugs encapsulated with the first biological agent. The second set of nano-carriers may further include the second biological agent in contact with one or more of the one or more drugs and the first biological agent. The first set of nano-carriers exhibits a rapid dissolution rate and may penetrate the intima layer exhibiting a burst release of the one or more drugs. As a result, a rapid dissolution rate and immediate drug effect may be achieved to address an acute thrombus formation. The second set of nano-carriers may have a slow dissolution rate and may penetrate one or more of the media layer and the adventitia layer exhibiting a prolonged in-tissue release of the one or more drugs. Due to the slow dissolution rate, a prolong drug effect may be achieved to address a sub-acute and late thrombus formation. Any combination of the different sets of the nano-carriers having varying average diameters, different biological agents and either an anti-thrombogenic agent or an anti-inflammatory agent may be used to achieve a particular therapeutic objective without departing from the scope of the invention.

EXAMPLES

Example 1

Preparation of Nano-Carriers:

Lipoid E80 was obtained from LIPOID GMBH, Batch No.: 1032466-03/916, and tricalcium phosphate hydrate, (in the form of a nanopowder with average particle size of about 200 nm (BET)) was obtained from Sigma Aldrich, Batch No.: 08811BJ. Dexamethasone was obtained from Sigma Aldrich, Batch no.: 068K1332 as per USP specification with purity greater than 99.0%. A polyamide catheter system with COPAN Co-Polyamide angioplasty balloon (herein after referred to as "the balloon system") coated with Hydraflow® Hydrophilic coating (hereinafter referred to as "the hydrophilic surface") was obtained from Minvasys, Paris, France.

Figure 2:
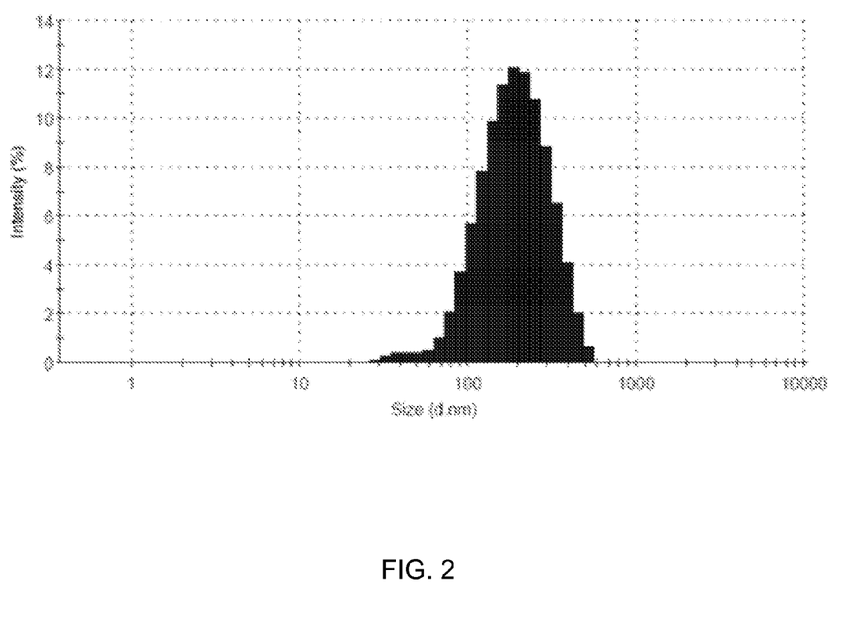
FIG. 2 illustrates size distribution of nano-particles of Lipoid E-80 in accordance with Example 1.

Lipoid E80 (20 mg w/w) was added to de-ionized water (10 ml) followed by Tween 80 (5 mg) to obtain an aqueous solution of Lipoid E80. The aqueous solutions of lipoid E80 (10 ml) was subjected to a high speed homogenization at 15000 to 20000 rpm for 20 to 25 minutes in an ice-cold water bath to obtain solution A1. The solution A1 thus obtained contained nano-particles of Lipoid E80. The solution A1 was analyzed for detecting particle size of the nano-particles using Malvern Zeta Sizer (ZS90) [Malvern, UK] size detector. FIG. 2 illustrates the size distribution of nano-particles of Lipoid E-80. The average diameter of the nano-particles of Lipoid E80 was found to be 165.51 nm.

Dexamethasone (20 mg w/w) was added to 10 ml of de-ionized water to obtain an aqueous solution of dexamethasone. The aqueous solution of dexamethasone (10 ml) was subjected to a high speed homogenization at 15000 to 20000 rpm for 150 to 200 minutes in an ice-cold water bath to obtain solution A2. The solution A2 thus obtained contained nano-crystals of dexamethasone. The solution A2 was subsequently analyzed for detecting particle size using Malvern Zeta Sizer (ZS90) [Malvern, UK] size detector.

Figure 3:
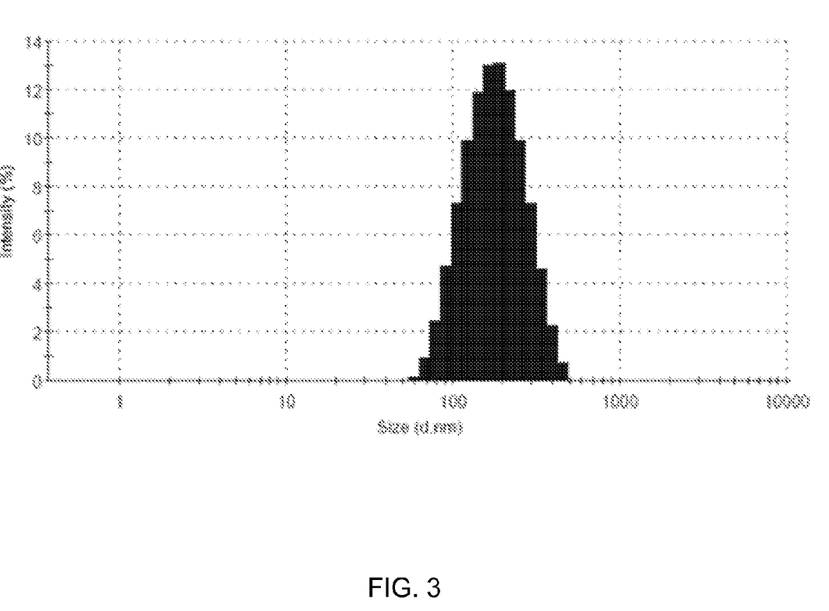
FIG. 3 illustrates size distribution of nano-carriers contained in solution A3 in accordance with Example 1.

The solution A2 was taken in a container. Then, the solution A1 was gradually added (drop by drop) to the container. The resultant mixture was subjected to high speed homogenizations at 15000 to 20000 rpm for 20 minutes to obtain 20 ml of solution A3. The solution A3 was homogenized again for 10 minutes. Thereafter, the solution A3 was stirred with a magnetic stirrer (2MLH hot plate heater cum stirrer, Accumax, INDIA) for 20 minutes. The solution A3 thus obtained contained nano-crystals of dexamethasone encapsulated with nano-particles of Lipoid E80. The solution A3 was subsequently analyzed for particle size detection using Malvern Zeta Sizer (ZS90) [Malvern, UK] size detector. FIG. 3 illustrates the size distribution of nano-carriers contained in solution A3. The average diameter of the nano-carriers contained in the solution A3 was found to be 157.02 nm.

Solution A3 (Aqueous solution of the nano-carriers containing lipoid E80 and Dexamethasone) was further subjected to extraction with dichloromethane. Solution A3 (20 ml) was transferred to 100 ml separating funnels respectively. 50 ml of dichloromethane was added to the 100 ml separating funnel. The resultant mixture was shaken for 15 minutes and then allowed to stand. Thereafter, two layers i.e., an aqueous layer and the dichloromethane layer were observed in the 100 ml separating funnel. The dichloromethane layer was separated from the aqueous layer. To the dichloromethane layer i.e., solution of the nano-carrier was added 0.2 mg/ml tricalcium phosphate hydrate to obtain solution A4. Solution A4 was stored in amber colored small measuring flasks with batch number. Subsequently, solution A4 thus prepared was used for coating a balloon system.

Example 2

Preparation of the Drug-Eluting Insertable Medical Device:

The solution of the nano-carriers i.e., solution A4 (1.9 ml) was fed into reservoir of a coating machine. A balloon system (Yangtze μ: 3.00*15 mm) was mounted on a rotating mandrel of the coating machine. The balloon system was exposed to an atomization nozzle of the coating machine. The balloon system was rotated at about 5 to 40 rpm by rotating the mandrel. Simultaneously, the solutions of nano-carriers were sprayed over the balloon system at 0.5 to 4.0 psi inert gas pressure and in two oscillations. Thus, the balloon system coated with the nano-carriers (hereinafter referred to as "the coated balloon system") was obtained. The coated balloon system was then removed and checked under high resolution microscope for the coating surface smoothness and any foreign particles.

Example 3

Detection of Amount of Drug Loaded on the Coated Balloon System:

The amount of dexamethasone loaded on the coated balloon system was quantified using a High Performance Liquid Chromatography (HPLC). The HPLC operating parameters were selected as: Flow Rate was set at 1.2 ml/min. (±0.01), λ-Maxima was set at 245 nm (±1 nm), Column Temperature was set at 30° C. (±2° C.), Sensitivity of a detector was set at 0.02 AUFS, injection volume was 20 μL and analysis time was set up to 20 minutes.

HPLC System [Analytical 2010 low pressure gradient equipped with an auto sampler (S 5200), an UV-Visible Detector (UV 2230), a HPLC pump (P2230) and (A 2000) Chromatography work station] was used for the HPLC analysis. The chromatography work station was used for the analysis at room temperature. Column—C18 [RP18 Length 4.6 mm×250 mm, particle size 5 μm] was attached with a column oven [PCI] for the heating. The samples were filtered through the millipore PTFE 0.45-micron syringe filter before the HPLC analysis to avoid any particulate matters. Pre-calibrated class A-grade volumetric flasks were used. Amber coloured glassware was used to protect against light. All the Qualigense solvents and reagents used were of HPLC grade. Dexamethasone of Batch No.: 776114-1/906 was obtained from Sigma Aldrich as per USP specification with purity greater than 99.0%. Mobile phase included Acetonitrile: Water in a concentration ratio of 50:50.

Dexamethasone (0.20 mg) was taken in a clean and dry 10 ml Standard Measuring Flask (SMF). The SMF was then filled up to mark with methanol and shaken for 5 to 10 minutes. The SMF was then kept in an ultrasonic cleaner and degassed for 10 minutes. The solution was then filtered through a 0.45 micron syringe filter to obtain a standard solution with "Standard Concentration" of 20 µg/ml.

Using the sample, vial 20 µL of the standard solution was injected in the HPLC system using an auto sampler and thereafter a chromatogram for the standard solution was obtained. Subsequently, the area of the peak for the standard solution ("Standard Area") was calculated. The retention time for the standard solution was found to be 3.063 minutes and the "Standard Area" corresponding to the peak for the standard solution was found to be 5023.78 mV*Sec.

For the quantification of the drug content loaded on the balloon system, the sample solution was prepared by inserting the coated balloon system in 10 ml SMF filled with methanol (10 ml). The SMF was then kept in an ultrasonic bath for 10 minutes to allow the dexamethasone present in the coated balloon system to completely dissolve in the methanol. Thus, the sample solution was obtained.

Using the sample vial of HPLC, the sample solution was injected in the HPLC injector and a chromatogram for the sample solution was obtained. Subsequently, the area of the peak for the sample solution ("Sample Area") was calculated. The retention time for the sample solution was found to be 3.499 minutes and the "Sample Area" corresponding to the peak for the sample solution was found to be 2951.45 mV*Sec. Subsequently, the amount of dexamethasone present on the coated balloon system was calculated using the following formula:

Amount of Drug (loaded on the coated balloon system)=(Sample Area/Standard Area)*(Standard Concentration/Sample Concentration)

Therefore, Amount of Drug=(2951.45/5023.78)*(20/(1/10))=117 µg

Thus, the Amount of Drug loaded the 3.00*15 mm coated balloon system was found to be 117 µg.

Various embodiments of the invention provide a drug-eluting insertable medical device and a method for treating Acute Myocardial Infarction, Thrombus Containing Lesion, and Saphenous Vein Graft Lesion. The invention also provides a drug-eluting insertable medical device and a method for addressing various phases of thrombus formation by achieving burst release and prolong in-tissue release of the anti-inflammatory and anti-thrombogenic agent. Moreover, the drug-eluting insertable medical device is polymer-free and is therefore not associated with any side effects that are exhibited by drug-eluting devices using polymers.

Those skilled in the art will realize that the above recognized advantages and other advantages described herein are merely exemplary and are not meant to be a complete rendering of all of the advantages of the various embodiments of the invention.

In the foregoing specification, specific embodiments of the invention have been described. However, one of ordinary skill in the art appreciates that various modifications and changes can be made without departing from the scope of the invention. Accordingly, the specification and figures are to be regarded in an illustrative rather than a restrictive sense, and all such modifications are intended to be included within the scope of the invention. The benefits, advantages, solutions to problems, and any element(s) that may cause any benefit, advantage, or solution to occur or become more pronounced are not to be construed as a critical, or required.

What is claimed is:

1. A method for delivering at least one drug at a target site in a blood vessel at two different rates, comprising:
   coating a surface of an insertable medical device with nano-crystals having an average diameter of approximately 157 nanometers, the nano-crystals comprising dexamethasone encapsulated with first nano-particles;
   the first nano-particles comprising egg lecithin with 80% phosphatidylcholine;
   coating the nano-crystals at least in part with second nano-particles, each of the second nano-particles in contact with either the dexamethasone or a nano-particle of the first nano-particles;
   the second nano-particles comprising tricalcium phosphate hydrate;
   implanting the insertable medical device coated with the nano-crystals at the target site in the blood vessel;
   wherein upon exposure to the target site in the blood vessel, the tricalcium phosphate hydrate of the second nano-particles dissolves immediately at a pH below 7.4 to provide a burst release of the dexamethosone, thereby exposing the first nano-particles to the target site in the blood vessel after the second nano-particles have dissolved; and
   wherein upon exposure to the target site in the blood vessel, the first nano-particles provide a prolonged release of the dexamethasone.

2. The method of claim 1, further comprising nano-crystals of a second drug selected from the group consisting of a dexamethasone, a genistine, a flavenoid, a neoflavone, a aurone, a chalcone, a dihydrochalcone, a flavonol, a dihydroflavonol, a flavone, a flavanol, a isoflavone, a anthocyanidin, a proanthocyanidin, a isoflavane, a heparin, and a beta-estradiol, a sulphated glycosaminoglycan, heparin, heparin sulphate, dermatan sulphate, chondroitin sulphate, a derivative or conjugate of sulphated glycosaminoglycan, an anti-thrombin, an anti-proliferative agent, metotrexate, mitomycin C, doxyrubicin, a somatostatin analog, cytoschalasin B, rapamycin, cyclosporin, glucocorticoid (e.g. dexamethasone, betamethasone), hirudin, a tocopherol, an angiopeptin, dexamethasone sodium phosphate, a thrombin modulator such as pyridine, pyridine N-oxide, methylprednisolone, sulfasalazine, vincristine, vinblastine, fluorouracil, doxorubicin hydrochloride, an anticoagulant, an antifibrin, an antithrombin, sodium heparin, a low molecular weight heparin, a heparinoid, hirudin, argatroban, forskolin, vapiprost, a prostacyclin, a prostacyclin analogue, dextran, a D-phe-pro-arg-chloromethylketone (synthetic antithrombin), dipyridamole, a glycoprotein IIIb/IIIa platelet membrane receptor antagonist, an antibody, a recombinant hirudin, bivalirudin, an angiopeptin, an antimitotic agent, and an oligonucleotide.

3. The method of claim 1, wherein the target site is at least one of a lesion and a thrombus in the blood vessel.

4. The method of claim 1, wherein the insertable medical device is one of a stent, a balloon, a balloon catheter, and a thrombus aspiration catheter.

5. An insertable medical device for delivering at least one drug at a target site in a blood vessel at two or more different rates comprising:
   a surface of the insertable medical device;
   nano-crystals having an average diameter of approximately 157 nanometers distributed on the surface, the nano-crystals comprising dexamethasone encapsulated with first nano-particles;
   the first nano-particles comprising egg lecithin with 80% phosphatidylcholine;
   second nano-particles, each of the second nano-particles in contact with either the dexamethasone or a nano-particle of the first nano-particles;
   the second nano-particles comprising tricalcium phosphate hydrate;

wherein upon exposure to the target site in the blood vessel, the tricalcium phosphate hydrate of the second nano-particles dissolves immediately at a pH below 7.4 to provide a burst release of the dexamethosone, thereby exposing the first nano-particles to the target site in the blood vessel after the second nano-particles have dissolved; and wherein upon exposure to the target site in the blood vessel, the first nano-particles provide a prolonged release of the dexamethasone.

6. The drug-eluting insertable medical device of claim 5, wherein the drug eluting insertable medical device is one of a stent, a balloon, a balloon catheter, and a thrombus aspiration catheter.

* * * * *